United States Patent [19]

Alon et al.

[11] Patent Number: 5,041,645

[45] Date of Patent: Aug. 20, 1991

[54] METHOD FOR THE PREPARATION AND RECOVERY OF ALKALI METAL CITRATES

[75] Inventors: Alexander Alon, Haifa, Israel; Philip W. Staal, Elkhart, Ind.

[73] Assignee: Haarmann & Reimer Corp., Springfield, N.J.

[21] Appl. No.: 282,909

[22] Filed: Dec. 12, 1988

Related U.S. Application Data

[63] Continuation of Ser. No. 732,658, May 10, 1985, abandoned.

[51] Int. Cl.$^5$ ............................................. C07C 59/265
[52] U.S. Cl. ..................................... 562/584; 522/580

[58] Field of Search ................................. 562/584, 580

[56] References Cited

PUBLICATIONS

Shen, JAOCS, vol. 61, No. 6 (Jun. 1984) pp. 1126–1130.

Primary Examiner—Bruce Gray
Attorney, Agent, or Firm—Jerome L. Jeffers

[57] ABSTRACT

Alkali metal citrates are prepared by the addition of an alkaline alkali metal base or salt to citric acid solutions and recovered in solid form by the addition of a $C_1$ to $C_5$ alcohol to the solution to cause precipitation.

7 Claims, No Drawings

METHOD FOR THE PREPARATION AND RECOVERY OF ALKALI METAL CITRATES

This is a continuation of application Ser. No. 732,658, filed May 10, 1985, now abandoned.

BACKGROUND OF THE INVENTION

Alkali metal salts of citric acid (particularly tri-sodium citrate) are useful in various products and processes such as ion exchange resin regeneration, cement retardation and electro as well as electroless plating.

Tri-sodium citrate dihydrate is also useful as a detergent builder and is a viable alternative to tripolyphosphate, the work horse of detergent builders, because it is nontoxic and readily biodegradable. However, the relatively high cost of this material has limited its acceptance by the detergent industry.

In the United States, citric acid is primarily produced by fungal fermentation of carbohydrates using selected strains of *Aspergillus niger*. This process results in the formation of citric acid-containing liquors which are impure materials containing sugars, salts, biomass, and up to about 85% by weight citric acid. Extensive purification is required to provide a citric acid product which is suitable for food and pharmaceutical specifications. These purification techniques increase the cost of the product while also providing a material which is of greater purity than that which is required for use as a detergent builder.

Shen, in JAOCS, Vol. 61, No. 6 (June 1984), describes a process for the recovery of an impure tri-sodium citrate which involves adding methanol to a hot solution of citric acid which has been converted to tri-sodium citrate by the addition of sodium hydroxide thereto to cause precipitation. The present invention was reduced to practice in the United States before the publication date of this article.

SUMMARY OF THE INVENTION

The present invention is a method for the recovery of solid alkali metal citrate which involves the steps of:
a) providing an aqueous solution of citric acid;
b) adding an alkaline alkali metal base or salt to the solution in sufficient quantity to convert the citric acid to alkali metal citrate and raise the pH of the solution to a level within the range of about 6.5 to 8.0;
c) adding an alcohol having 1 to 5 carbon atoms to the solution in an amount sufficient to provide a volume ratio of alcohol to the solution of at least about 3.7:1 to precipitate the alkali metal citrate; and
d) recovering the precipitated alkali metal citrate.

The alkaline base or salt can be added either before, after or simultaneously with the addition of the alcohol.

DESCRIPTION OF THE INVENTION

The aqueous solution of citric acid can be obtained from any adequate source or even prepared specifically for use in the recovery process. However, economic considerations suggest the use of citric acid mother liquor or fermentor beer. While the final product obtained from this process will not be sufficiently pure for food additive or pharmaceutical use, it is quite suitable for use with detergents. Citric acid solution is obtained during the manufacturing process by filtering the fermentor beer to remove biomass or using the mother liquor from the crystal filtration which is normally recycled back to the concentrator. A concentration of at least 50% by weight citric acid is preferred because yields may be uneconomically low with more dilute solutions.

The first process step involves adding an alkaline alkali metal base or salt to the citric acid solution in an amount sufficient to convert the citric acid to its corresponding tri-alkali metal citrate and to raise the solution's pH to a level of from about 6.5 to 8.0. This pH range is necessary because at a pH below about 6.5 the product will be less fully substituted than the desired tri-alkali metal citrate whereas above pH 8.0 the excess alkali metal is wasted, and tends to cause color bodies to form from the impurities. While alkali metal bases or salts having cations other than sodium may be used, the sodium cation is clearly preferred because of greater utility and economy of sodium citrate as compared to other alkali metal citrates such as the potassium salt. Suitable bases or salts include $Na_2CO_3$, $NaHCO_3$, KOH, $K_2CO_3$, $NH_4OH$, $(NH_4)_2CO_3$ and $KHCO_3$. NaOH is preferred because of its low cost and relatively low solubility as compared to the others. The alkali metal citrate is precipitated by the addition of an alcohol of from 1 to 5 carbon atoms to the solution prepared in the previous step. Suitable alcohols include primary alcohols such as ethanol and methanol as well as secondary alcohols such as isopropanol. While the temperature at which the alcohol is added is not critical, it is preferred that this step be carried out at an elevated temperature, typically up to the alcohol's reflux temperature, because larger more desirable crystals which do not tend to agglomerate are formed at these elevated temperatures.

It is essential to the efficient operation of this recovery technique that the alcohol be used in considerable excess and at least in an amount sufficient to provide a volume ratio of 3.7:1 alcohol to alkali metal citrate solution. Greater amounts of alcohol up to a ratio of 8:1 and more may be used. At ratios greater than 8:1, there is normally observed the precipitation of impurities and the economics of the process tend to be unfavorable. The large excess of alcohol is necessary to ensure maximum precipitation of product.

The addition of the alkali metal base or salt and alcohol to the citric acid or citrate solution can take place in any order or simultaneously, but it is preferred that the base or salt be added first to convert the citric acid to its corresponding alkali metal citrate and that this step be followed by the addition of the alcohol. Typically, the alcohol is added slowly to permit adequate time for crystal growth. The alcohol addition results in the precipitation of the citrate from solution by the formation of crystalline particles which can be recovered by conventional liquid/solid separatory techniques such as filtration or centrifugation. The recovered material is typically washed with additional alcohol and dried to provide a product suitable for use as a detergent builder or otherwise.

The method of practicing the present invention is further illustrated by the following examples.

EXAMPLE I

A 1 liter beaker was charged with 350 ml (462 g) citric acid process mother liquor containing 260.5 g citric acid and 201.5 g $H_2O$. While stirring, 325.9 g of 50% (w/w) NaOH solution was added to bring the pH to 6.6. The solution was heated to 78° C. and filtered to remove impurities. The hot solution was placed in a 5 liter, 3 neck round bottom flask fitted with a reflux condenser, stirrer and heating mantle. The solution was heated to 80° C. and 1500 ml (1184 g) ethyl alcohol was added at a rate of 30 ml per minute which resulted in the formation of a slurry of tri-sodium citrate crystals. The flask was heated to the ethanol's reflux temperature which provided better crystal formation.

The slurry of sodium citrate crystals in ethanol-water was cooled to 20° C. and filtered whereupon the crystals were washed with 150 ml (118 g) of ethanol and dried in a hot air oven at 50° C. The yield of tri-sodium citrate dihydrate was 83.6% of theory.

EXAMPLE II

A 1 liter beaker was charged with 141 g of $H_2O$ and 189 g of citric acid to simulate citric acid mother liquor. While stirring, 229.5 g of a 50% sodium hydroxide solution was added to bring the pH to 6.7. The solution was heated to 80° C. and filtered as before. The hot solution was placed in a 2 liter, 3 neck round bottom flask fitted with a reflux condenser, stirrer and heating mantle. A total of 1333 ml (1052 g) of ethyl alcohol was added over a 30 minute period while maintaining reflux to form a slurry of sodium citrate crystals.

The slurry of sodium citrate crystals was cooled to 20° C. and filtered whereupon they were washed with ethanol and dried in an air oven at 50° C. to yield 264.3 g of tri-sodium citrate dihydrate which was 94.7% of theory.

The ethyl alcohol was recovered from the simulated mother liquor by distilling to a head temperature of 85° C. The recovery was 1134 g which was 99% of theory.

EXAMPLE III

A 30 gallon stainless steel tank was charged with 39.5 pounds of sodium citrate and 40 pounds of deionized water. A total of 131 pounds of ethyl alcohol was added over a 30 minute period while maintaining the temperature shown in the Table below. The batch was cooled to 50° C. and then filtered. The filter cake was washed with ethyl alcohol and dried in an air oven at 50° C. The dried sodium citrate was weighed and the percentage of crystals larger than 80 mesh was determined by sieve analysis. The yield of greater than 80 mesh material is shown in the Table below from which it can be determined that crystal size is directly proportional to the temperature during ethanol addition.

| Temperature During Ethanol Addition | Yield Greater Than 80 Mesh |
|---|---|
| 50° C. | 52% |
| 60° C. | 88% |
| 70° C. | 94% |

EXAMPLE IV

A 1 liter beaker was charged with 330 g of citric acid mother liquor containing 183 g of citric acid and 47 g of water. While stirring, 234 g of a 50% NaOH solution was added to bring the pH to 7.1. The solution was heated to 80° C. and passed through a preheated sintered glass Buchner funnel to remove extraneous solids.

The hot solution was transferred to a 2 liter 3 neck flask fitted with a reflux condenser and feed funnel. The flask was heated to 77° C. whereupon 1046 g of isopropyl alcohol was slowly added over a period of 30 minutes while maintaining the contents of the flask at reflux temperature (approximately 80° C.).

The slurry of sodium citrate crystals which formed during the addition of isopropanol was cooled to 20° C. and filtered after which the filter cake was washed with 85 g of fresh isopropanol and dried in an air oven at 50° C. for 12 hours. The yield of tri-sodium citrate dihydrate was 71% of theory. The product was identified as the dihydrate by conducting a moisture analysis using the Karl Fisher method. The theoretical moisture level for the dihydrate is 12.25%. The actual water content found was between 11.8 and 12.3%.

The filtration mother liquor/wash liquor was distilled in a glass distillation unit at atmospheric pressure to a head temperature of 81° C. to recover 1038 g or 92% of the isopropanol used.

What is claimed is:

1. A method for the recovery of solid sodium, potassium or ammonium tri-citrate which comprises the steps of:
    a) providing an aqueous solution of citric acid;
    b) adding $Na_2Co_3$, $NaHCO_3$, KOH, $K_2CO_3$, $NH_4OH$, $(NH_4)_2CO_3$ or $KHCO_3$ to the solution in sufficient quantity to convert the citric acid to tri-sodium, potassium or ammonium citrate thereby raising the pH of the solution to a level within the range of about 6.5 to 8.0;
    c) adding an alcohol having 1 to 5 carbon atoms to the solution in an amount sufficient to provide a volume ratio of alcohol to the solution of at least about 3.7 to 1 to precipitate the sodium, potassium, or ammonium citrate; and
    d) recovering the precipitated sodium, potassium or ammonium citrate.

2. The method of claim 1 wherein the alkali metal or ammonium containing base or salt is $Na_2Co_3$, $NaHCO_3$, KOH, $K_2CO_3$, $NH_4OH$, $(NH_4)_2$ or $KHCO_3$.

3. The method of claim 1 wherein the alkali metal or ammonium containing base or salt is NaOH.

4. The method of claim 1 wherein the alcohol is ethanol.

5. The method of claim 1 wherein the solution is maintained at the reflux temperature of the added alcohol.

6. The method of claim 1 wherein the ratio of alcohol to the solution is in the range of from about 3.7:1 to 8.0:1.

7. A method for the recovery of solid tri-sodium citrate dihydrate which comprises the steps of:
    a) providing an aqueous solution of citric acid containing at least 50% citric acid on a weight basis;
    b) adding NaOH to the solution in sufficient quantity to convert the citric acid to tri-sodium citrate and raise the pH of the solution to a level of from about 6.5 to 8.0;
    c) adding ethanol to the solution in an amount sufficient to provide a volume ratio of alcohol to the solution of from about 3.7:1 to 8:1 while maintaining the solution at the reflux temperature of the ethanol to precipitate the tri-sodium citrate;
    d) recovering the precipitated tri-sodium citrate by liquid/solid separatory techniques; and
    drying the recovered tri-sodium citrate sufficiently to form the dihydrate.

* * * * *